US 8,110,082 B2

(12) United States Patent
Thundat et al.

(10) Patent No.: US 8,110,082 B2
(45) Date of Patent: *Feb. 7, 2012

(54) PHOTOELECTROCHEMICAL MOLECULAR COMB

(75) Inventors: Thomas G. Thundat, Knoxville, TN (US); Thomas L Ferrell, Knoxville, TN (US); Gilbert M. Brown, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1198 days.

This patent is subject to a terminal disclaimer.

(21) Appl. No.: 11/731,952

(22) Filed: Apr. 2, 2007

(65) Prior Publication Data

US 2007/0175760 A1    Aug. 2, 2007

Related U.S. Application Data

(60) Division of application No. 10/365,242, filed on Feb. 12, 2003, now Pat. No. 7,211,181, which is a continuation-in-part of application No. 10/077,633, filed on Feb. 15, 2002, now Pat. No. 7,090,757.

(51) Int. Cl.
*G01N 27/453* (2006.01)
*H01L 31/00* (2006.01)

(52) U.S. Cl. ........................... 204/606; 136/263

(58) Field of Classification Search .................. 204/600, 204/450, 606, 456; 136/263
See application file for complete search history.

(56) References Cited

U.S. PATENT DOCUMENTS

| | | | |
|---|---|---|---|
| 5,151,741 A | 9/1992 | Kakutani et al. | |
| 5,500,188 A | 3/1996 | Hafeman et al. | |
| 5,985,568 A | 11/1999 | Krihak et al. | |
| 6,053,035 A * | 4/2000 | Nomura et al. | 73/86 |
| 6,203,985 B1 | 3/2001 | Jiang et al. | |
| 6,475,728 B1 | 11/2002 | Martin et al. | |
| 6,706,473 B1 | 3/2004 | Edman et al. | |
| 6,730,208 B1 | 5/2004 | Bruel | |
| 7,090,757 B2 * | 8/2006 | Thundat et al. | 204/450 |

FOREIGN PATENT DOCUMENTS

WO    WO 00/13784    3/2000

OTHER PUBLICATIONS

Gurtner et al., "Photoelectropheretic Transport and Hybridization of DNA Oligonucleotides on Unpatterned Silicon Substrates", Journal of The American Chemcial Society, vol. 122, pp. 8589-8594 (2000).
Inoue et al., "Chemical-Imaging Sensor Using Enzyme", Sensors and Actuators B, Elseevier Sequoia S.A., vol. B32, pp. 23-26 (1996).
Brown et al., "Development and Characterization of a Titantium Dioxide-Based Semiconductor Photoelectrochemical Detector", Analytical Chemistry Society, vol. 64, pp. 427-434 (1992).
Owicki et al., "The Light-Addressable Potentiometric Sensor: Principles and Biological Applications", Annual Review of Biophysics and Biomolecular Structure, vol. 23, pp. 87-113 (1994).

* cited by examiner

*Primary Examiner* — Alex Noguerola
(74) *Attorney, Agent, or Firm* — Joseph A. Marisco; Judson R. Hightower (57) ABSTRACT

A method, system, and apparatus are provided for separating molecules, such as biomolecules. The method, system, and apparatus utilize an electrochemical cell having at least two electrodes, one electrode comprising a photo-sensitive material capable of generating a photopotential. Molecules are moved through an electrolyte medium between the at least two electrodes based upon localized photopotentials.

17 Claims, 4 Drawing Sheets

PHOTOELECTROCHEMICAL MOLECULAR COMB

CROSS REFERENCE TO RELATED APPLICATION

This application claims priority to U.S. application Ser. No. 10/077,633, filed Feb. 15, 2002, the disclosure of which is incorporated herein by reference in its entirety.

STATEMENT REGARDING FEDERALLY SPONSORED RESEARCH

The invention was made with government support under contract DE-AC05-00OR22725, awarded by the United States Department of Energy to UT-Battelle, LLC, the United States Government has certain rights in this invention.

TECHNICAL FIELD

The invention generally relates to the molecular characterization of molecules. Specifically, the invention relates to fractionation of heterogeneous mixtures of particles or molecules on the basis of characteristics such as size and/or charge and also the analysis of electrochemical properties of particles.

BACKGROUND

Analysis of a sample of biological origin frequently requires the separation of mixtures of biomolecules, such as nucleic acids, proteins, and polypeptides, which often have limited sample size. Electrophoresis, in which charged molecules move in a liquid under the influence of an electric field, has long been the method of choice for separating many classes of biomolecules. This method takes of advantage of differing migration velocities, $v_{ep}$, of different molecules.

The migration velocity, $v_{ep}$, is the distance (L) a molecule or particle moves per unit time (t). The migration velocity is the product of the electrophoretic mobility, $\mu_{ep}$, multiplied by the electric field strength E (units of volts/cm):

$$v_{ep} = \mu_{ep} \times E \quad \mu_{ep} = q/6\pi\eta R$$

where q is the charge on the particle and $\eta$ is the viscosity of the medium and R is the radius of the particle. The velocity is, thus, directly proportional to the charge on the particle and the field strength and inversely proportional to the size of the particle and the viscosity of the medium. For relatively large particles or biomolecules, the charge increases as the size of the molecule increases, and the charge to mass (or radius) ratio becomes nearly constant. Under these circumstances if the electrophoresis is carried out in the presence of a gel composed of agarose (agarose gel electrophoresis) or crosslinked polyacrylamide (polyacrylamide gel electrophoresis), the gel structure creates a molecular sieving effect that allows the molecules or particles to be separated on the basis of size.

Capillary gel electrophoresis is typically carried out in 50 μm diameter capillaries that are 10 cm to 1 m long with a field strength that is generally in the range of 100 V/cm to 500 V/cm, and requires a high-applied voltage greater, typically greater than 1 KV. Heat generation is directly proportional to the square of the applied voltage, and the voltages required to achieve separation in capillary electrophoresis may cause degradation of sensitive samples.

A subject of a considerable amount of research in recent years has been microscale fluid handling systems that perform fast, automated, high-resolution sample preparation, reaction, and separation. Currently, this is being accomplished through advances in microfluidics. The idea is that once the manipulation of fluids can be mastered on the microscale, key experiments for biomolecule separation and analysis can be integrated and automated—all on a mass-produced chip. In microfluidic-based devices, nucleic acid molecules, proteins, polypeptides and other such molecules are transported, manipulated, and separated through miniature channels embedded into the chip. Detection systems can also be integrated into the chip or affixed externally as a separate component for seamless, automated and highly sensitive detection.

SUMMARY

The invention provides an apparatus, comprising a photo-sensitive electrode; an electrolyte medium in contact with the photo-sensitive electrode; a counter electrode; and a voltage source. The voltage source is electrically coupled to the photo-sensitive electrode and the counter electrode such that when a voltage is applied to the electrodes a depletion region is generated in the photo-sensitive electrode. At least one photon energy source incident upon the depletion region, wherein the photon energy source generates photon energy such that photon energy contacting the depletion region forms electron-hole pairs, wherein either or both of the photon energy source and/or photo-sensitive electrode is movable relative to the other. In one aspect of the invention the photo-sensitive electrode is a semi-conductive material. The semi-conductive electrode may be selected from the group consisting of Si, Ge, GaAs, TiO2, CdS, and ZnO. In another aspect of the invention the photon energy source produces a beam of light to create a localized photopotential in the electrolyte medium. In yet another aspect of the invention the photon energy source is moved relative to the photo-sensitive electrode. The voltage applied to the electrodes may be reversed or alternated in order to reverse the electric field between the electrodes intermittently. In one aspect of the invention, the counter electrode is optically transmissive and electrically conductive.

The invention also provides a method for separating molecules. The method comprises applying a voltage to a photo-sensitive electrode and a counter electrode to generate a depletion region on the photo-sensitive electrode, wherein the electrodes are separated by an electrolyte medium in contact with the photo-sensitive electrode, wherein the electrolyte medium comprises a plurality of analytes. The depletion region is then contacted with a photon energy source, wherein the photon energy source generates photon energy such that photon energy contacting the depletion region forms electron-hole pairs that are separated by the potential to form a photopotential. The photon energy source is moved relative to the semiconductive surface such that a photopotential is propagated across the photo-sensitive electrode and proximal to the location of the analytes thereby causing the analytes to migrate relative to the photopotential. IN one aspect of the invention the analytes comprise biomolecules such as polynucleotides, oligonucleotides, proteins, polypeptides, and/or peptides. The molecules may be detectably labeled with agents known in the art including, for example, a radioisotope, a dye, a fluorescent molecule, a luminescent molecule, and/or an enzyme.

The details of one or more embodiments of the invention are set forth in the accompanying drawings and the descrip-

DESCRIPTION OF DRAWINGS

Like reference symbols in the various drawings indicate like elements.

DETAILED DESCRIPTION

The invention provides an apparatus, system and method for manipulating charged biomolecules using photon energy. The invention utilizes electrical potentials and photopotentials to move biomolecules on or within an electrolyte medium (e.g., an ionically conductive medium).

The invention provides a microscale method for performing chemical separation of biomolecules such as polynucleotides, oligonucleotides, proteins, polypeptides, and peptides on a chip using photoelectrochemistry. Advantageously, the invention provides a method of separation and analysis that requires neither miniature channels nor capillary tubes for the separation and analysis of the same class or complex mixtures of biomolecules. However, the apparatus, system, and methods of the invention may be combined with further analytical systems including microfluidic chips known in the art. The combination of the methods and systems of the invention are used for a first degree of separation and further analytical processes are then used for further characterization, if needed.

The photoelectrochemical molecular comb technology disclosed herein utilizes electrokinetics and semiconductor photoelectrochemistry to create a spatially confined electric field on a microchip, which is used to transport and separate biomolecules without the use of channels. This innovative technology has the potential to provide substantial cost and performance advantages for users, including minimizing the amount of the sample required, minimizing the time for processing, increasing analysis flexibility and complexity, and improving separation resolution.

The invention provides a general light-directed method for separating molecules. This objective is accomplished by creating a localized photovoltage that moves analyte molecules, as opposed to creating a static field gradient. The methods and apparatus of the invention provide an advantageous and compact system for the separation of biomolecules and particles.

Generally, a pair of electrodes (anode and cathode) are maintained in contact with an electrolyte medium by, for example, direct immersion in the electrolyte medium. The electrodes are immersed in the electrolyte medium to allow a desired voltage gradient to be maintained across, for example, a porous substrate or gel when a direct current power source is attached to the electrodes.

The external electric field applied between the electrodes causes positively charged cations to migrate toward the negatively charged electrode, or cathode, and negatively charged anions to migrate toward the positively charged anode. In this manner, analytes move toward the anode or cathode under the influence of the electric field. In the absence of any other influences, the analytes will travel through the electrolyte medium as discrete zones, or bands, based on differences in solute mobility.

In the simplest mode of electrophoresis, free solution or zone electrophoresis, a buffer solution consists solely of an electrolyte medium. Analytes are separated purely on differences in the electrophoretic velocity of analytes due to their charge-to-size ratios.

By modulating electrical and photopotential between electrodes, biomolecules such as proteins and/or polynucleotides either seek out, or avoid, regions of high ionic current, depending upon their charge characteristics. Thus, by changing the location of the high-ionic current on a semiconductive electrode surface by utilizing photon energy, control over the movement of charged biomolecules can be accomplished. The spatial and temporal modulation of potential between the electrodes (e.g., a semiconductive electrode and counter electrode) through the use of external photon energy (e.g., light) provides the basis to control the electrokinetic forces and the movement of such charged biomolecules as polypeptides, oligonucleotides, and polynucleotides.

A biomolecule includes any number of various molecules. For example a molecule or analyte of interest may be a nucleic acid (e.g., DNA or RNA), a polypeptide (e.g., an antibody, protein, enzyme), a biochemical (e.g., a lipid, hormone, fatty acids, carbohydrate), pharmaceuticals, a chemical such as organics including, for example, alkanes, alkenes, alkynes, dienes, alicyclic hydrocarbons, arenes, alcohols, ethers, ketones, aldehydes, cyclic hydrocarbons, carbonyls, carbanions, polynuclear aromatics and derivatives of such organics, e.g., halide derivatives, so long as the molecule has an overall net positive or negative charge.

To understand the principle of this methodology, it will be helpful to briefly review photoelectric properties of semiconductors, or more specifically, those of an ES structure formed by an electrolyte solution (E); and a semiconductor (S). The photoelectric characteristics of this structure are closely related to those of a standard Metal-Semiconductor (MS) device, which is described in S. M. Sze, "The Physics of Semiconductors", 2nd Edition, Chapt. 7 (Wiley Interscience 1981), the contents of which are incorporated herein by reference.

Space-charge regions of small but finite thickness form at a semiconductive/electrolyte interface in the presence of a bias potential. In the case of the ES structure, an effective bias, in the form of a junction potential, is present under all but very special conditions. A space-charge region forms in response to the distance dependence of charge density on the semiconductor. This produces an electric potential gradient that changes the energy of the semiconductor's valence and conduction bands ("band bending") in the vicinity of the interface. This condition in turn reflects the fact that, while there is a bias potential across the interface, there is no net charge transfer at the interface when equilibrium is reached.

In the presence of a reverse bias, the valence and conduction band edges of an n-doped semiconductor bend upward near the interface and electrons flow out of the interfacial region in response to the corresponding potential gradient. As a result, a majority carrier depletion layer is formed in the vicinity of the interface. Light absorption in the semiconductor provides a mechanism to create electron-hole pairs within this depletion layer/region. The electron-hole pairs are split by the locally acting electric field, and a corresponding photocurrent flows. It is this latter effect that allows for the movement of charged biomolecules in the electrolyte medium.

Band bending can be achieved by suitably polarizing the semiconductor with respect to the electrolyte medium using a power supply. The back contact to the semiconductor electrode is Ohmic in character while the semiconductor-electrolyte medium interface acts as a Schottky barrier. Therefore, most of the applied voltage is dropped at the semiconductor-electrolyte medium interface creating a space charge (depletion or accumulation) layer in the semiconductor. The formation of a depletion or accumulation layer depends on the bias and the type of semiconductor (i.e., n-type or p-type). The nature of band bending can be changed from depletion to accumulation by changing the sign of the applied voltage with respect to the flat band potential of the semiconductor-electrolyte interface.

Proper biasing of the semiconductor-electrolyte interface results in the subsequent creation of a charge-depletion layer in the semiconductor. Irradiation of the semiconductor-electrolyte medium interface with photons of appropriate energy produces electron-hole pairs in the depletion or accumulation layer. The electric field in the depletion layer separates the electron-hole pairs. For example, for an n-type semiconductor, the bands are bent upwards for a depletion layer, and therefore electron vacancies (i.e., holes) come to the semiconductor-electrolyte interface during illumination. In the case of an accumulation layer irradiation causes the electrons to accumulate weakly at the solid-electrolyte interface. Irradiation of the spot containing the biomolecules with a focused beam of photons of energy greater than the band gap of the photo-sensitive semiconductive electrode generates new charge carriers in the charge-depletion layer. The thereby-separated charge carriers reach the interface of the semiconductor and electrolyte and create a localized photovoltage.

The depletion layer present on the semiconductor exhibits electrical characteristics similar to those of a capacitor with a voltage-dependent capacitance. Illumination serves to lower the impedance of the depletion layer.

The ES structure can also comprise an oxide layer between the semiconductor and the electrolyte medium. The oxide layer will pass current only above a characteristic ("threshold") frequency.

This effective reduction of the ES impedance also depends on the light intensity, which determines the rate of generation of electron-hole pairs. In the absence of significant recombination, the majority of photogenerated electrons flow out of the depletion region and contribute to the photocurrent.

This light-induced surface-charge dependence may be used to induce the lateral displacement of charged biomolecules between fully exposed and partially masked regions of the interface. As the illumination intensity is increased, the fully exposed regions will correspond to the regions of interface of lowest impedance, and hence of highest current, and biomolecules will be drawn into these regions.

Additionally, time-varying changes in the illumination pattern can be used to affect the motion of the biomolecule. For example, charged biomolecules move in response to the change in photopotential provided by the photon energy contacting the depletion region of the semiconductor. If a focused beam of photon energy is scanned to an adjacent spot on the photo-sensitive semiconductive electrode, the biomolecule will move along with the photon energy because the biomolecule will be attracted to this new region having a change in current or photopotential. Where the electrolyte medium comprises a sieve or gradient, this movement of biomolecules results in the separation of the biomolecules based upon size or other physical/chemical characteristics, a process analogous to gel electrophoresis. By adjusting the speed at which the photon energy beam moves to a different location on the semiconductor surface, biomolecules can be separated with precision. Thus, an electrolyte medium that is capable of separating molecules based upon more than one physical/chemical characteristic may be used wherein movement of a biomolecule in one direction separates the biomolecule based upon one characteristic while movement in a another direction (e.g., perpendicular to the first) separates the biomolecules based upon a second characteristic.

Figure 1:
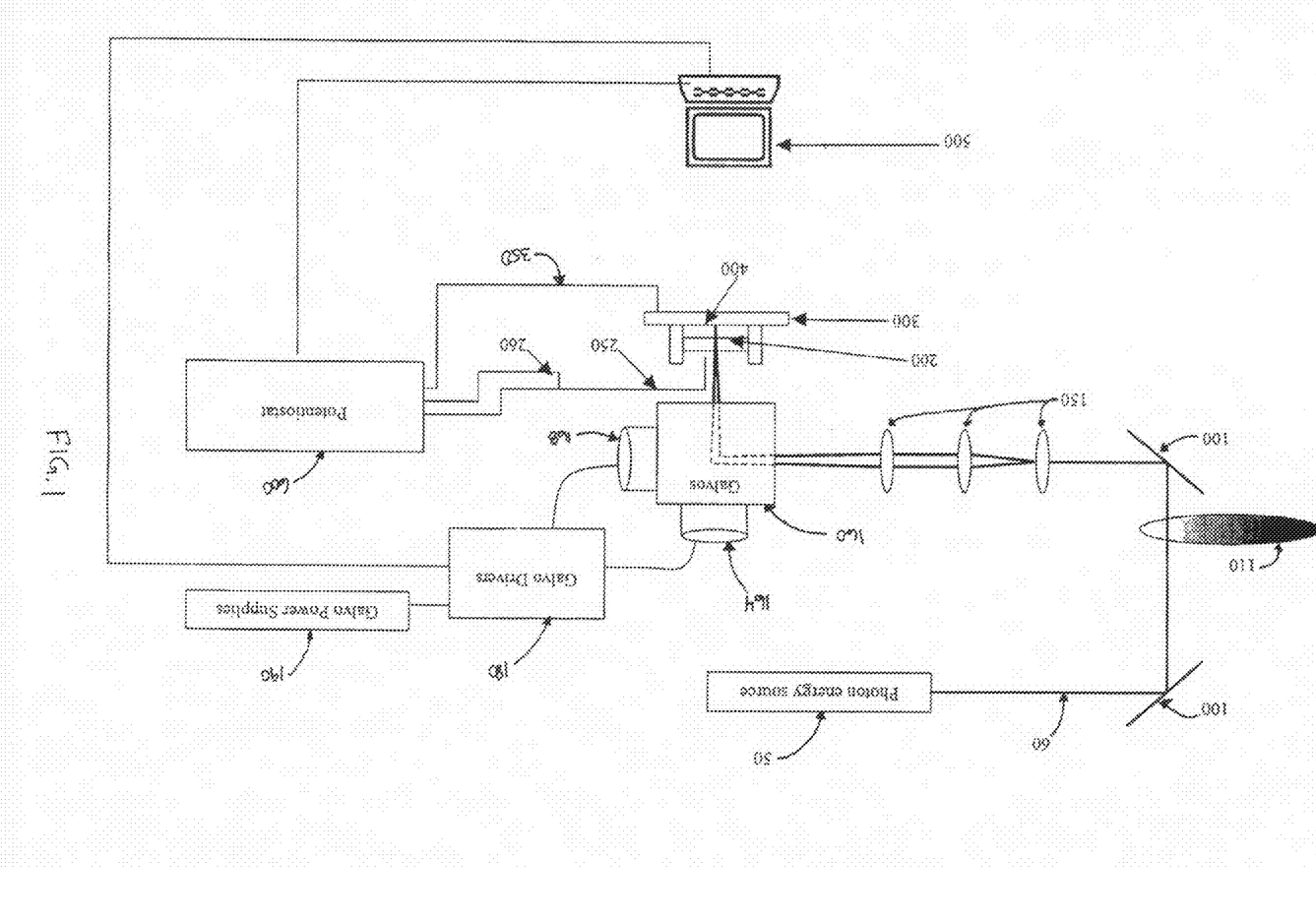
FIG. 1 is a schematic of an apparatus of the invention.

Turning now to FIG. 1, an apparatus, system, and method of the invention utilize an electrolyte medium 400 (e.g., an ionically conductive medium) sandwiched between a photo-sensitive semiconductive electrode 300 and a counter electrode 200. A power supply 600 (e.g., a potentiostat) is connected by wires 250 and 350 to the electrodes 200 and 300, respectively. The power supply 600 provides voltage to generate a potential difference between the electrodes 200 and 300 and across the electrolyte medium 400. The electrolyte medium 400 comprises analyte molecules to be analyzed and/or separated.

Figure 2A:
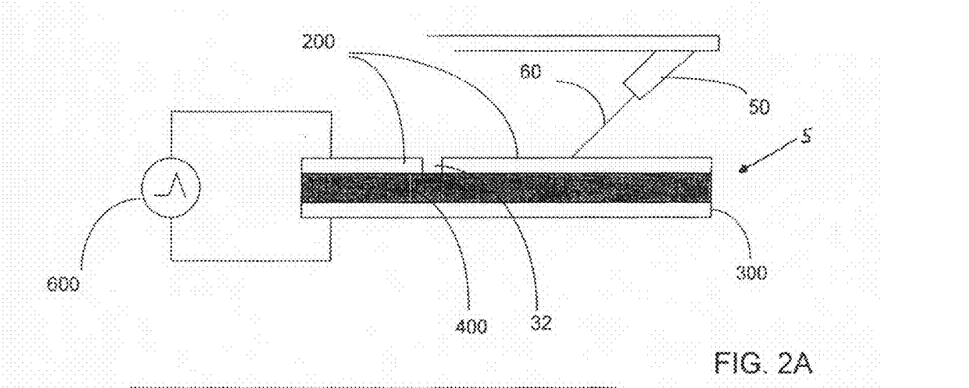
FIG. 2 collectively shows an electrochemical cell of the apparatus of FIG. 1.
Figure 2B:
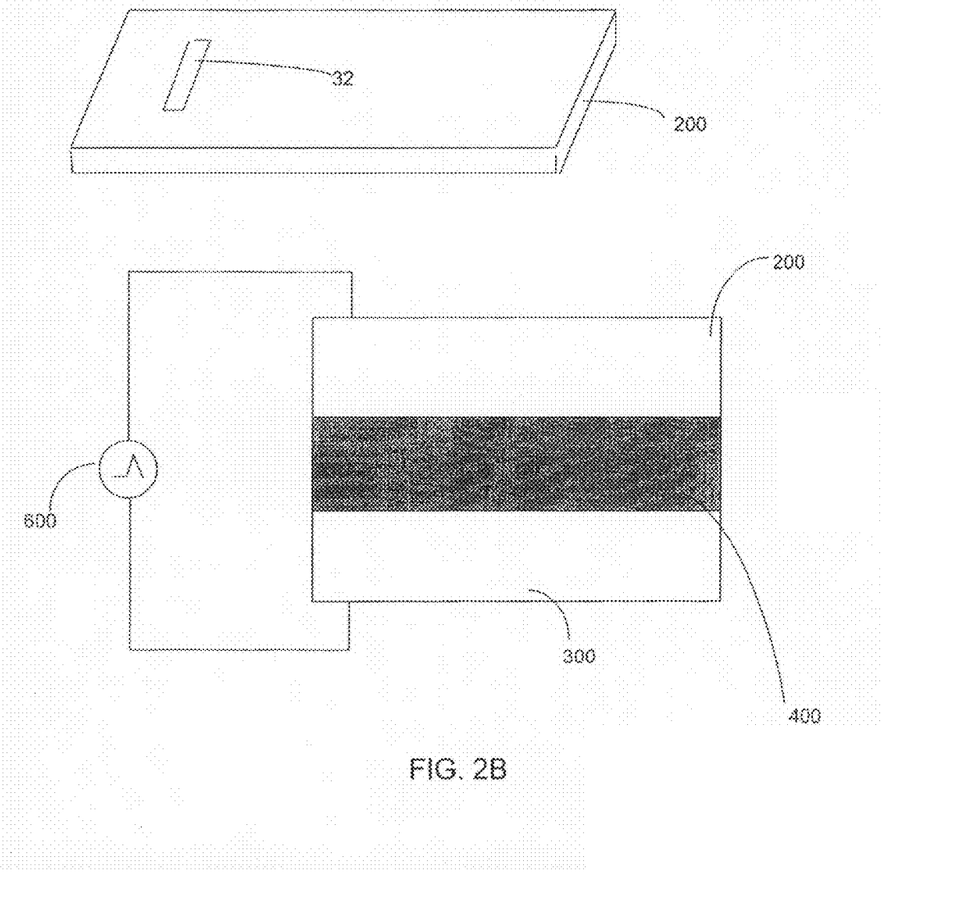

The electrodes 200 and 300 and the electrolyte medium 400 form an electrochemical cell (generally depicted by 5 in FIGS. 2A and B). The electrodes 200 and 300 are positioned relative to one another such that when voltage is applied an electric field is generated between the electrodes. In one aspect of the invention the electrodes are planar and parallel and are separated from one another to define a gap of about 20-50 μm, about 50-100 μm, about 100 μm to 1 mm, about 1-2 mm, or about 2-3 mm.

FIG. 2 shows an electrochemical cell of the invention in more detail. The electrochemical cell includes a photo-sensitive semiconductive electrode 300, an electrolyte medium 400, and a counter electrode 200. In one aspect of the invention, an inlet port 550 can be used to load the electrolyte medium 400 into the space between the electrodes. The inlet port 550 may also be used to load a sample to be analyzed.

The counter electrode 200 is typically semi-transparent (e.g., phototransmissive). An example of a suitable counter-electrode is indium tin oxide (ITO) deposited on a glass substrate. The counter electrode may also include a silane layer that prevents analyte biomolecules from adhering to the electrode. Other transparent or semi-transparent materials can be used, such as quartz with a thin layer of a conductive material, such as gold, other inorganic conductors, or combinations of conductive materials.

The photo-sensitive semiconductive electrode 300 can be formed with a p-type or n-type material known in the art, such as Si, Ge, GaAs, CdS, ZnO, $TiO_2$, and the like (see Table 1). Other semiconductive materials are discussed in the compendium *Semiconductor Electrodes*, H. Finklea, ed., Elsevier, N.Y., 1988, which is incorporated herein by reference in its entirety. One example of a photo-sensitive semiconductive electrode is an Si electrode. In one aspect of the invention, the semiconductor (e.g., the Si) may also include an oxide layer (e.g., a SiOx layer). The photo-sensitive semiconductive electrode can be fabricated from a 1 inch-square portion of a Si (100) wafer, typically 200-250 μm thick, n-doped to typically 0.01 Ohm cm resistivity. In one aspect the Si (100) wafer may be capped with a thin oxide of typically 30-40 Å in thickness. A thick oxide layer can be obtained by growing under standard conditions in a furnace at 950° C., which can be etched to obtain a desired structure. Alternatively, a thin oxide layer may be regrown on a previously stripped surface of (100)- orientation under UV light. UV oxide growth provides the ability to pattern the surface by placing a quartz mask representing the desired pattern in the path of the UV light and thereby generating a chemically homogeneous topographically flat surface. To avoid particle adsorption to the surface of the photosensitive electrode, clean conditions should be used. For example, the photo-sensitive semiconductive electrode is cleaned prior to contacting an electrolyte medium to ensure that the voltage potential can be applied across the photo-sensitive semiconductive electrode and the electrolyte medium interface. Oxides on a Ge substrate can be cathodically reduced or removed, for example, using a mild etching solution.

TABLE 1

Some Elemental and Compound Semiconductors For Photoelectrochemical Application

| Semiconductor | Conductive Type(s) | Optical Band Gap Energy [eV] |
|---|---|---|
| Si | n, p | 1.11 |
| GaAs | n, p | 1.42 |
| GaP | n, p | 2.26 |
| InP | n, p | 1.35 |
| CdS | n | 2.42 |
| CdSe | n | 1.70 |
| CdTe | n, p | 1.50 |
| $TiO_2$ | n | 3.00 (rutile) |
|  |  | 3.20 (anatase) |
| ZnO | n | 3.35 |

An ohmic contact is electrically connected to the photo-sensitive semiconductive electrode 300 in order to maintain the integrity of the potential applied across the photo-sensitive semiconductive electrode/electrolyte medium interface. An ohmic contact is typically a metal-semiconductor contact with a linear current-voltage characteristic and low resistance. Such ohmic contact materials are known in the art. Thus, as a result of the low electrical resistance of the ohmic contact, the voltage applied across the electrolyte medium 400 is dropped in the depletion layer. Accordingly, the voltage applied can be less than 10 volts or as high as 1 kv or more.

Also depicted in FIG. 1 is a photon energy source 50. The photon energy source can be any type of light source that emits a focused beam of photon energy 60 (e.g., light) or which may be modified using various filters 110, mirrors 100, lens 150, and/or apertures to direct a focused beam of photon energy 60. Filters make it possible to adjust the luminous power to values of less than, equal to, or greater than the necessary threshold. For example, a helium-neon laser with output of 5 mW at 632.8 nm may be used. Such a laser source provides about 500 μW of power near a target analyte biomolecule. In one aspect of the invention, the beam of light may be modified to obtain a desired geometric shape such as a focused point, a focused line of a millimeter or less in length, a curved "parenthetical shaped" geometry, and the like. Accordingly, photon energy sources include laser diodes or light emitting diodes that emit light in the visible or very near-infrared wavelength ranges.

The photon energy source 50 will typically provide a focused point of intense light so that the photon energy arriving at the interface is highly localized. In one aspect of the invention, the photon energy 60 is pulsed so that no saturation phenomenon occurs. The magnitude of the photovoltage induced is related to the light intensity and the extent of the band bending. The latter can be controlled by adjusting the biasing voltage. In one embodiment, the biasing is kept constant to maintain a depletion region in the semiconductor. The bias is selected such that the photovoltage is maximized. In one embodiment of the invention, a potential between the photo-sensitive electrode 300 and counter electrode 200 can also be alternated in such a way that the potential is alternated between the electrodes (typically in the dark, "light off," phase). This causes the analyte molecule (e.g., a biomolecule) motion to alternate between the photo-sensitive electrode 300 and the counter electrode 200, and thus inhibits the analyte molecules from collecting on the surface of either of the electrodes.

In order to scan the photon energy source across the photo-sensitive electrode 300 the beam of photon energy 60 or the photo-sensitive electrode 300 are moved relative to one or the other or both to each other. As depicted in FIG. 1 a Galvos 160 is used to focus the photon energy 60 to various points on the photo-sensitive electrode 300. The Galvos comprises automated means 164 and 168 for positioning the beam of photon energy 60 in an X and Y plane. In another aspect of the invention, the Galvos and/or the photo-sensitive semiconductive electrode may be located on a Z-stage that further allows focusing of the beam of light in a Z-plane. In yet another aspect of the invention, the electrochemical cell comprising the photo-sensitive semiconductive electrode is located on an automated X-Y stage or an automated X-Y-Z stage. The automated stage allows for the automation of the scanning of the beam of photon energy upon the photo-sensitive semiconductive electrode. In another aspect, a pivotally mounted mirror can be used to direct the photon energy (e.g., light beam) across (e.g., at various coordinates of) the photo-sensitive electrode. In another aspect of the invention an array of photon energy beams can be used to move multiple molecules or samples comprising molecules across the photo-sensitive electrode. Such an array of photon energy beams can be generated by splitting one photon energy beam into multiple beams or by utilizing multiple photon energy sources.

Figure 4:
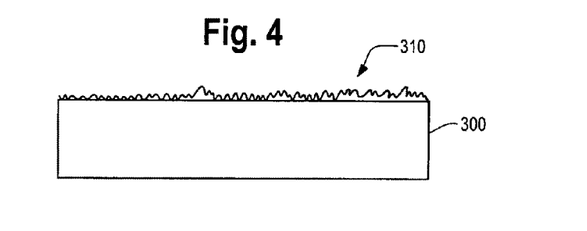
FIG. 4 is a diagram showing the modified surface of a photo-sensitive electrode of the invention useful in separating molecules.

The electrolyte medium 400 typically comprising, for example, a TRIS buffer. In one embodiment, the electrolyte medium further comprises a gel including, for example, polyacrylamide (e.g., cross-linked polyacrylamide), agarose, dextran, and the like, containing electrolyte and buffered substances, which are brought into contact with the photo-sensitive semiconductive electrode and the counter electrode. The electrolyte medium and/or gel may be a few microns to a few millimeters thick (e.g., about 20-50 μm, about 50-100 μm, about 100 μm to 1 mm, about 1-2 mm, or about 2-3 mm thick). The electrolyte medium may contain analyte molecules (e.g., proteins, polypeptide, peptides, polynucleotides, oligonucleotides, and the like) to be separated or analyzed at the time of placing the electrolyte medium in contact with the electrode(s). Alternatively, the analyte molecules may be added to the electrolyte medium after the electrolyte medium is contacted with the electrode(s). Techniques for forming "wells" or sample reservoirs in various gel media such as agarose and polyacrylamide for receiving analyte molecules are known in the art. In addition, various physical characteristics of gel media (e.g., agarose or polyacrylamide gels) can be modified to effect the rate and movement of analyte molecules. For example, changing the percentages of agarose or acrylamide in the electrolyte medium will change the rate of movement and thus the type of separation that can be accomplished between analyte molecules of different sizes. In another aspect of the invention separation can be accomplished by patterning the surface of the photo-sensitive semi-conductive electrode (See FIG. 4).

The apparatus, system and method thus includes an electrolyte medium 400 sandwiched between the photo-sensitive semiconductive electrode 300 and the counter electrode 200 to complete an electrical circuit between the electrodes. When the photo-sensitive semiconductive electrode is in contact with an electrolyte medium 400, and a voltage is applied to the electrodes such that a double layer of charge (dipole layer) is established at the interface.

As shown in FIG. 3, when a voltage is applied to the electrodes 200 and 300, a potential is generated between the electrodes and across the electrolyte medium 400. The potential bends the conduction and valence bands 36 and 38 in the photo-sensitive electrode 300. Bending of the conduction band 36, below the Fermi level 40 for the photo-sensitive electrode 300 creates a depletion region 18. The depletion region 18 can provide a source of electrons or holes to create a photopotential in the electrolyte medium 400.

Figure 3A:
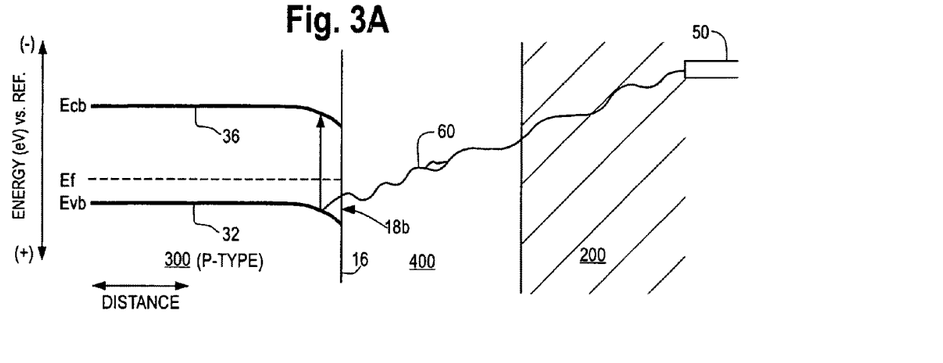
FIG. 3 shows an energy diagram at the interface between a photo-sensitive electrode and an electrolyte medium during operation of the apparatus of FIG. 1. Ecb is the conduction band; Evb is the valence band and Ef is the Fermi level.

With reference to FIGS. 3A and B, the photon energy source 50, such as a laser, having an emission energy level greater than the voltage potential across the photo-sensitive electrode-electrolyte interface directs photon energy 60 at the depletion region 18a or accumulation region 18b in the photo-sensitive electrode 300. The photon energy source 50 produces, for example, a line (or point) of intense light across the width of the depletion or accumulation region. As a result, the electrons (when using a p-type semiconductive material; FIG. 3A) from the generated electron-hole pairs are localized at the interface. When using an n-type semiconductive material (FIG. 3B) the holes are accumulated at the interface.

Figure 3B:
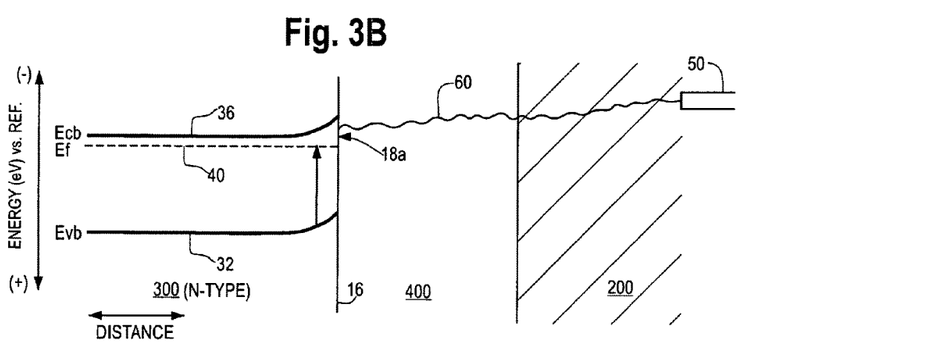

The photon energy source 50 raises the energy level of the photo-sensitive electrode 300 at the interface with the electrolyte medium 400 above the Fermi level to create electron-hole pairs in the depletion region which are separated by the pre-existing potential between the electrodes 200 and 300. The separated electrons and holes have opposite charges, which cause the electrons to move in a direction opposite of the holes. By proper choice of the semiconductive material of the photo-sensitive electrode (e.g., p-type or n-type) and counter electrode (anode or cathode), either the electron or holes of the electron-hole pairs can be brought to the interface with the electrolyte medium 400 to generate a photopotential. For example, where a p-type material is used, the electrons of the electron-hole pairs move to the photo-sensitive electrode/electrolyte medium interface.

The direction of the photoelectrophoresis action is to the irradiated spot on the semiconductor electrode. In one aspect of the invention, a reversing potential is applied between the two electrodes during a "light-off" cycle of the repetitive pulses. This moves the molecules in the opposite direction so they can again be attracted to the semiconductor when the focused laser beam is moved to an adjacent spot. When a line of instantaneous photopotential is created between the photo-sensitive semiconductive electrode and counter electrode, the analyte molecules move towards the counter electrode. Since the photon energy can be incrementally stepped to a different location in the depletion region of the photo-sensitive semiconductive electrode, biomolecules are incrementally attracted to the current flux at the different location and thereby are moved incrementally through the electrolyte medium with an overall direction parallel to the two electrodes. The biomolecules move in the same direction as the incremental stepping of the photon energy beam. Interaction of the biomolecules with a gel matrix of the electrolyte medium results in the separation of molecules of varying sizes of, for example, polymer length and/or molecular weight.

It may be desirable to prevent biomolecules present in an electrolyte medium between two electrodes from contacting either electrode. In order to avoid contact of the biomolecule in the electrolyte medium with either electrode, applied voltage to the electrodes may be intermittent or reversed at periodic intervals. In yet another aspect, a combination of periodic or reversed voltage and intermittent photon energy may be used.

FIG. 1 also shows a programmable computer 500. The various techniques, methods, and aspects of the invention described above can be controlled in part or in whole using computer-based systems and methods. Additionally, computer-based systems and methods can be used to augment or enhance the functionality described above, increase the speed at which the functions can be performed, and provide additional features and aspects as a part of or in addition to those of the invention.

The programmable-computer system can include a main memory, preferably random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage media represents a floppy disk magnetic tape, optical disk, etc., which is read by and written to by removable storage drive. As will be appreciated, the removable storage media includes a computer usable storage medium having stored therein computer software and/or data.

In alternative embodiments, secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM, or PROM) and associated socket, and other removable storage units and interfaces which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, etc. Software and data transferred via a communications interface are in the form of signals which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

Computer programs useful for monitoring or managing the apparatus and systems of the invention are typically present on computer program medium. A computer readable medium includes media such as a removable storage device, a disk capable of installation in a disk drive, and signals on a channel. These computer program products are means for providing software or program instructions to a computer systems.

Computer programs (also called computer control logic) are stored in main memory and/or secondary memory. Computer programs can also be received via a communications interface. Such computer programs, when executed, enable the computer system to perform the features of the present invention as discussed herein. In particular, the computer programs, when executed, enable the processor to perform the methods outlined in above. Accordingly, such computer programs represent controllers of the system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implemented using a combination of both hardware and software.

Transport of biomolecules has been demonstrated when applying voltages less than 1 KV. Semiconductors such as Si, Ge, GaAs, $TiO_2$, CdS, and ZnO in contact with a liquid exhibit a change in surface charge upon irradiation with light of an appropriate wavelength when electronic bands of the semiconductors are bent. These reactions occur initially by the absorption of photons of energies greater than the corresponding semiconductor band gap energy to form conduction band electron-valence band hole pairs.

The following examples are provided to demonstrate a particular aspect of the invention and should not be construed to limit the invention.

EXAMPLES

A counter electrode was prepared by thermally evaporating onto a glass slide (1 inches by 3 inches), 2.5 nm of chromium and 25 nm Gold on one surface of the slide. An AWG 26 wire was attached to the chromium/gold using silver epoxy and connected to a Model 173 potentiostat/galvanostat (EG&G Princeton Applied Research).

A photo-sensitive semiconductive electrode of Germanium (n-type; <0.4 Ω-cm; 1-1-1 orientation; 2"Φ; 14 mil thick) was obtained from Polishing Corp. of America (part#Ge2N111SSP). An ohmic contact was provided using a gallium indium eutectic 99.99% (Alfa Aesar #12478)—diamond scribe to scratch the surface. Epoxy was used to connect an AWG 26 wire to the electrode, which was in turn connected to a Model 173 potentiostat/galvanostat (EG&G Princeton Applied Research).

The counter electrode and semiconductive electrode were arranged in a cell having an inner diameter of about 4 cm and a height of about 6 mm. A Tris-glycine buffer (6.25 mM Trizma base, 62.5 glycine, pH 8.6) was used to cover a 1% (w/v) agarose gel. The gel thickness is 1.85 mm. The gap between the two electrodes is about 6 mm (e.g., 1.85 mm gel plus 4 mm Tris-buffer).

Bovine serum albumin, lysozyme, β-amylase, and/or rabbit IgG were labeled with Marina Blue, an amine-reactive blue-fluorescent dye having an absorbance at 362 nm and an emission at 459 nm. (Molecular Probes, cat. # M-10165). A mineral lamp (366 nm) was used to visualize the biomolecules (UVP Model UVGL-58).

Figure 5:
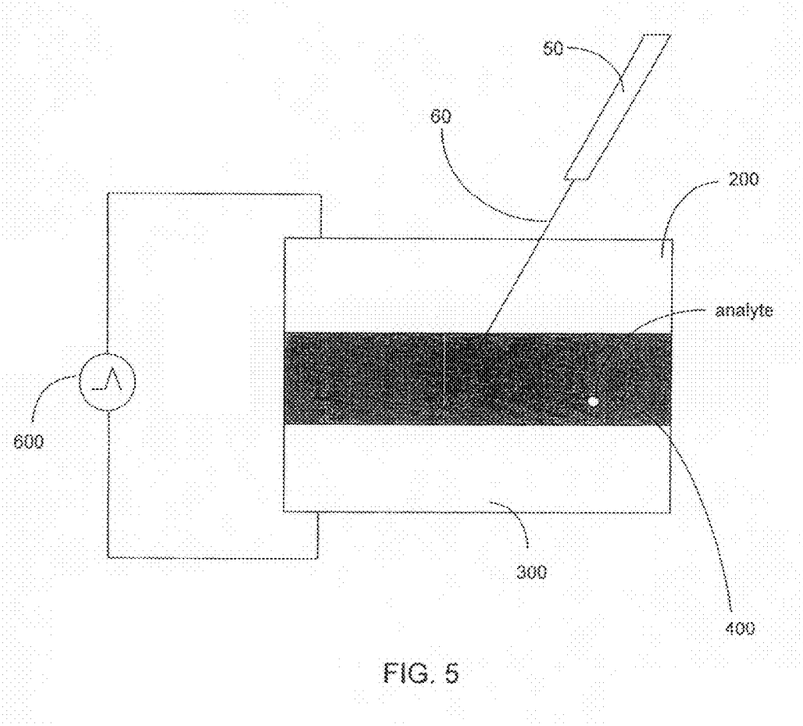
FIG. 5 is a diagram showing the movement of a biomolecule within the electrolyte solution as the potential is alternated between the electrodes.

Using current control the electrode current was set to −0.235 mA (approx. 3.2V) on the potentiostat. The current was cycled at various times. Visualization of the blue-labeled biomolecule showed movement of the biomolecule in a verticle zig-zag motion as the current of the potentiostat was cycled and as the laser was scanned from one end of the gel to the other. FIG. 5, shows a representation of the overall movement of a labeled bovine serum albumin molecules as the laser was scanned and the current cycled.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus, comprising:
a photo-sensitive electrode;
an electrolyte medium in contact with the photo-sensitive electrode;
a counter electrode;
a voltage source electrically coupled to the photo-sensitive electrode and the counter electrode, wherein a voltage generates a depletion region in the photo-sensitive electrode; and
at least one photon energy source incident upon the depletion region, wherein the photon energy source generates photon energy such that photon energy contacting the depletion region forms electron-hole pairs, wherein either or both of the photon energy source and/or photo-sensitive electrode is movable relative to the other wherein the counter electrode is substantially planar and parallel to the photo-sensitive electrode.

2. The apparatus of claim 1, wherein the photo-sensitive electrode is a semi-conductive material.

3. The apparatus of claim 2, wherein the semi-conductive material is selected from the group consisting of Si, Ge, GaAs, $TiO_2$, CdS, and ZnO.

4. The apparatus of claim 1, wherein the electrolyte medium is a film.

5. The apparatus of claim 4, wherein the film comprises a composition selected from the group consisting of polyacrylamide, agarose, polymethyl methacrylate, and dextran.

6. The apparatus of claim 1, wherein the counter electrode comprises a conductive inorganic material.

7. The apparatus of claim 1, wherein the photon energy source produces a beam of light to create a localized photopotential in the electrolyte medium.

8. The apparatus of claim 1, wherein the photon energy source produces a beam of a desired geometry.

9. The apparatus of claim 1, wherein the photon energy source is intermittent.

10. The apparatus of claim 1, wherein the photon energy source is moved relative to the photo-sensitive electrode.

11. The apparatus of claim 1, wherein the voltage source comprises a potentiostat.

12. The apparatus of claim 1, wherein the voltage is modulated.

13. The apparatus of claim 1, wherein the surface of the photo-sensitive electrode is artificially patterned.

14. The apparatus of claim 1, wherein the voltage is alternated to generate an alternating pulsed potential between the electrodes.

15. An apparatus, comprising:
a photo-sensitive electrode;
an electrolyte medium in contact with the photo-sensitive electrode;
a counter electrode;
a voltage source electrically coupled to the photo-sensitive electrode and the counter electrode, wherein a voltage generates a depletion region in the photo-sensitive electrode; and
at least one photon energy source incident upon the depletion region, wherein the photon energy source generates photon energy such that photon energy contacting the depletion region forms electron-hole pairs, wherein either or both of the photon energy source and/or photo-sensitive electrode is movable relative to the other wherein the counter electrode comprises a conductive organic material.

16. The apparatus of claim 15, wherein the counter electrode is optically transmissive and electrically conductive.

17. An apparatus, comprising:

a photo-sensitive electrode;

an electrolyte medium in contact with the photo-sensitive electrode;

a counter electrode;

a voltage source electrically coupled to the photo-sensitive electrode and the counter electrode, wherein a voltage generates a depletion region in the photo-sensitive electrode; and at least one photon energy source incident upon the depletion region, wherein the photon energy source generates photon energy such that photon energy contacting the depletion region forms electron-hole pairs, wherein either or both of the photon energy source and/or photo-sensitive electrode is movable relative to the other wherein the counter electrode comprises a mixed inorganic/organic conductor.

* * * * *